(12) United States Patent
Schlather et al.

(10) Patent No.: US 11,351,101 B2
(45) Date of Patent: Jun. 7, 2022

(54) NAIL POLISH REMOVING COMPOSITION

(71) Applicant: L'ORÉAL, Paris (FR)

(72) Inventors: Andrea E. Schlather, New Providence, NJ (US); Aline Aude Guimont, South Orange, NJ (US); Daniella Cristina Gonzalez-Toro, Hoboken, NJ (US)

(73) Assignee: L'ORÉAL, Paris (FR)

(*) Notice: Subject to any disclaimer, the term of this patent is extended or adjusted under 35 U.S.C. 154(b) by 0 days.

(21) Appl. No.: 16/176,130

(22) Filed: Oct. 31, 2018

(65) Prior Publication Data

US 2020/0129403 A1   Apr. 30, 2020

(51) Int. Cl.

| | | |
|---|---|---|
| *C11D 3/40* | (2006.01) | |
| *C11D 7/02* | (2006.01) | |
| *C11D 7/50* | (2006.01) | |
| *A61K 8/49* | (2006.01) | |
| *A61Q 3/04* | (2006.01) | |
| *A61K 8/34* | (2006.01) | |
| *A61K 8/25* | (2006.01) | |
| *A61K 8/19* | (2006.01) | |
| *A61K 8/29* | (2006.01) | |
| *C11D 7/26* | (2006.01) | |
| *C11D 3/14* | (2006.01) | |
| *C11D 7/20* | (2006.01) | |

(52) U.S. Cl.
CPC .............. *A61K 8/4973* (2013.01); *A61K 8/19* (2013.01); *A61K 8/25* (2013.01); *A61K 8/29* (2013.01); *A61K 8/34* (2013.01); *A61K 8/345* (2013.01); *A61Q 3/04* (2013.01); *C11D 3/14* (2013.01); *C11D 3/40* (2013.01); *C11D 7/20* (2013.01); *C11D 7/261* (2013.01); *C11D 7/264* (2013.01); *C11D 7/267* (2013.01); *C11D 7/5004* (2013.01)

(58) Field of Classification Search
CPC .... C11D 3/14; C11D 3/40; C11D 7/20; C11D 7/5004; C11D 7/267; C11D 7/261; C11D 7/264
USPC ................................ 510/118, 397, 505, 504
See application file for complete search history.

(56) References Cited

U.S. PATENT DOCUMENTS

| | | | | |
|---|---|---|---|---|
| 4,197,212 A | * | 4/1980 | Minton ................. | A61K 8/042 106/170.27 |
| 5,342,536 A | * | 8/1994 | Miner .................... | A61K 8/345 134/38 |
| 6,028,040 A | * | 2/2000 | Jarema .................... | A61K 8/37 510/118 |
| 6,841,523 B1 | * | 1/2005 | Holtz ...................... | A61K 8/34 510/118 |

(Continued)

FOREIGN PATENT DOCUMENTS

| | | |
|---|---|---|
| CN | 105520857 A | 4/2016 |
| CN | 106619390 A | 5/2017 |

*Primary Examiner* — Gregory R Delcotto
(74) *Attorney, Agent, or Firm* — Meagher Emanuel Laks Goldberg & Liao, LLP

(57) ABSTRACT

The invention relates to compositions for removing nail polish comprising a solvent and a high load of colorant, preferably between 0.5 wt % and 5.0 wt %. Preferably, the composition has an absorption peak in a range between 460 nm and 600 nm, and a normalized extinction of at least 0.5 for at least one wavelength in the range when measured in an optically transparent solvent via spectrophotometer and across 1 cm path length in a ratio of 1:8 composition to optically transparent solvent. Methods of removing nail polish are also provided.

7 Claims, 3 Drawing Sheets

(56) References Cited

U.S. PATENT DOCUMENTS

| | | | |
|---|---|---|---|
| 2004/0028637 A1 | 2/2004 | Villard et al. | |
| 2004/0142830 A1* | 7/2004 | Tavares | A61K 8/37 510/118 |
| 2008/0196174 A1 | 8/2008 | Schmenger et al. | |
| 2012/0315231 A1* | 12/2012 | Lin | A61Q 3/04 424/61 |
| 2013/0319462 A1* | 12/2013 | Cifelli | A61K 8/4973 134/6 |
| 2016/0354295 A1* | 12/2016 | Macneill | C11D 3/1206 |
| 2018/0023038 A1* | 1/2018 | Hunt, Jr | C11D 3/2093 510/111 |

* cited by examiner

NAIL POLISH REMOVING COMPOSITION

FIELD OF THE INVENTION

The present invention relates to nail polish remover compositions, and specifically to nail polish remover compositions that incorporate high loads of colorant.

BACKGROUND

Nail polish compositions are typically designed to provide long-lasting color to nails. Because of the materials used in nail polish compositions to obtain the desired properties, it has proven difficult to remove such nail polish compositions from nails without adversely affecting the nails or leaving a visible indication of removal process.

As such, it is desirable to provide an efficacious nail polish remover that minimizes the impact on the nails and reduces the fear that some users have of spent nail polish contacting the skin.

BRIEF SUMMARY

The inventors have recognized that small concentrations of colorants can be used in prior art formulas for the purpose of masking 'yellowing' of the rest of the formula that manifests over time.

As such, the present invention is drawn to nail polish removers that incorporate a solvent and a high load of one or more colorants, typically between 0.5 wt % and 5.0 wt %. The nail polish removers may include other materials, such as a thickening agent or an abrasive agent.

Advantageously, the nail polish removers have an absorption peak that falls between 460 nm and 600 nm. The nail polish removers may have a normalized extinction of at least 0.5 for at least one wavelength in the range when measured in an optically transparent solvent via spectrophotometer and across 1 cm path length in a ratio of 1:8 composition to optically transparent solvent (one part nail polish remover composition by weight out of eight, or 12.5% in water). The nail polish removers may have an extinction of at least 1.5 when measured across all wavelengths in the entire visible spectrum in an optically transparent solvent via spectrophotometer and across 1 cm path length in a ratio of 1:8 composition to optically transparent solvent.

In certain embodiments, at least one colorant has an absorbance peak at a wavelength between 390 nm and 700 nm. In certain embodiments, the nail polish remover utilizes a solvent that is an acetone, an acetate, a low carbon alcohol, or a high boiling point ester, while in other embodiments, the nail polish remover is substantially free of acetone.

The present invention is also drawn to a method of removing nail polish, involving applying the disclosed nail polish remover composition and allowing the remover to remain in contact with a coated nail for a time sufficient to loosen the coating from the nail, then separating the coating and the composition from the nail.

DETAILED DESCRIPTION

Figure 1:
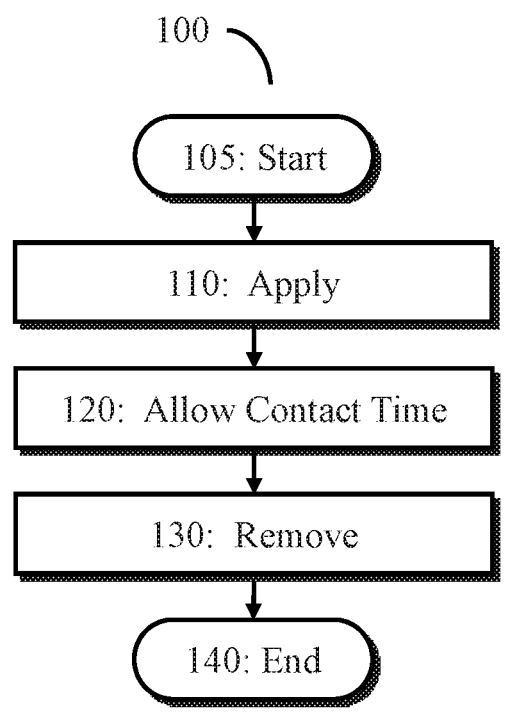
FIG. 1 is a flowchart of the method for removing nail polish.

As used herein, articles such as "a" and "an" when used in a claim, are understood to mean one or more of what is claimed or described.

As used herein, the expression "at least one" means one or more and thus includes individual components as well as mixtures/combinations. All percentages listed are by weight unless otherwise noted.

As used herein, the term "about [a number]" is intended to include values rounded to the appropriate significant digit. Thus, "about 1" would be intended to include values between 0.5 and 1.5, whereas "about 1.0" would be intended to include values between 0.95 and 1.05.

As used herein, the term "at least one" means one or more and thus includes individual components as well as mixtures/combinations.

As used herein, the terms "include", "includes" and "including" are meant to be non-limiting.

As used herein, the term "normalized" is used to indicate that all spectra are arbitrarily defined to have a maximum optical density of 1 and a minimum optical density of 0 for those in the range from 400-800 nm.

As used herein, "substituted" means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

As used herein, "nail" includes fingernails as well as toenails.

In accordance with the present invention, compositions for removing nail polish are disclosed, where the nail polish removing composition comprises at least one solvent and at least one colorant at a concentration of between 0.5 wt % to 5.0 wt % are provided.

Solvents

According to some embodiments, the compositions of the present invention includes at least one solvent chosen from organic and inorganic solvents. The solvents can be present in a proportion preferably of up to 99.9% by weight, relative to the total weight of the composition, and more preferably from 20% to 98% by weight.

Preferred solvents may include, but are not limited to, liquid ketones at ambient temperature such as methylethylketone, methylisobutylketone, diisobutylketone, isophorone, cyclohexanone and acetone, liquid alcohols at ambient temperature such as ethanol, isopropanol, diacetone-alcohol, 2-butoxyethanol and cyclohexanol, liquid glycols at ambient temperature such as ethyleneglycol, propyleneglycol, pentyleneglycol and glycerol, liquid propyleneglycol ethers at ambient temperature such as propyleneglycol monomethylether, propyleneglycol monomethyl ether acetate and dipropyleneglycol mono-n-butylether, short-chain esters (comprising in total from 3 to 8 carbon atoms) such as ethyl acetate, methyl acetate, propyl acetate, n-propyl acetate, iso-propyl acetate, n-butyl acetate, iso-butyl acetate, ter-butyl acetate and isopentyl acetate, liquid alkanes at ambient temperature such as decane, heptane, dodecane and cyclohexane, liquid aromatic hydrocarbons at ambient temperature such as toluene and xylene, liquid silicones at ambient temperature, and mixtures thereof.

Compositions may also comprise volatile and/or non-volatile solvents. The term "volatile solvent" refers to a solvent capable of evaporating on contact with keratin matter, in less than one hour, at ambient temperature and at atmospheric pressure. Conversely, a "non-volatile solvent" evaporates on contact with keratin matter in more than one hour, at ambient temperature and atmospheric pressure.

In some embodiments, the compositions comprise a solvent chosen from acetone, ethyl acetate, propyl acetate, butyl acetate, isopropyl alcohol, or some combination thereof.

In some embodiments, the compositions comprise a solvent chosen from acetone, an acetate, a low carbon alcohol, a high boiling point ester, or some combination thereof.

In accordance with the present invention, compositions for removing nail polish, where the nail polish removing composition comprises at least one low carbon alcohol are provided. "Low carbon alcohol" means an alcohol containing from 1 to 8 carbon atoms. The low carbon alcohol may contain from 2 to 6 carbon atoms, such as from 2 to 5 carbon atoms. Examples of low carbon alcohols include, but are not limited to, ethanol, propanol, butanol, pentanol, isopropanol, isobutanol, and isopentanol.

In certain embodiments, the at least one low carbon alcohol may be present in the compositions of the present invention in an amount greater than 5% by weight, such as greater than 10% by weight, such as greater than 15% by weight, such as greater than 20% by weight and such as less than 50% by weight, including all ranges and subranges therebetween such as, for example, from 5% to 50%, from 10% to 50%, from 15% to 50%, from 20% to 50%, from 10% to 40%, from 15% to 30%, etc., with all weights being based on the weight of the composition.

In accordance with the present invention, compositions for removing nail polish, where the nail polish removing composition comprises at least one high boiling point ester are provided. "High boiling point ester" means an ester having a boiling point greater than 90° C. The high boiling point ester may have a boiling point greater than 125° C., such as greater than 175° C., and such as greater than 200° C. Examples of high boiling point esters include, but are not limited to, esters of C4-C22 dicarboxylic or tricarboxylic acids and of C1-C22 alcohols, such as C1-C8 alcohols, and such as C1-C3 alcohols. Notable high boiling point ester compounds include carbonate esters, adipates, sebacates and succinates. Specific examples of high boiling point ester compounds include, but are not limited to, alkylene carbonates such as propylene carbonate, dimethyl succinate, diethyl succinate, dimethyl glutarate, diethyl glutarate, dimethyl sebacate, diethyl sebacate, diisopropyl sebacate, bis(2-ethylhexyl) sebacate, dimethyl adipate, diisopropyl adipate, di-n-propyl adipate, dioctyl adipate, bis(2-ethylhexyl) adipate, diisostearyl adipate, ethyl maleate, bis(2-ethylhexyl) maleate, triisopropyl citrate, triisocetyl citrate, triisostearyl citrate, trioctyldodecyl citrate and trioleyl citrate.

The at least one high boiling point ester compound may be present in the compositions of the present invention in an amount greater than 10% by weight, such as greater than 15% by weight, such as greater than 20% by weight and such as less than 50% by weight, including all ranges and subranges therebetween such as, for example, from 10% to 50%, from 15% to 50%, from 20% to 50%, from 10% to 40%, from 15% to 30%, etc., with all weights being based on the weight of the composition.

According to other embodiments of the present invention, the compositions for removing nail polish may be "essentially free" of acetone, water or both, "substantially free" of acetone, water, or both, or "free" of acetone, water or both. "Essentially free" means that the composition contains less than about 3% of the identified ingredient. "Substantially free" means that the composition contains less than about 2% of the identified ingredient. "Free" means that the composition contains less than 1% of the identified ingredient. A composition containing "no water" or "no acetone" contains about 0% of the identified ingredient. In certain other embodiments of the invention, the concentration of water may be less than about 20% by weight, such as less than about 15% by weight, less than about 10% by weight in the composition.

Colorants

According to embodiments of the present application, compositions comprising at least one colorant are provided. Suitable colorants include, but are not limited to, lipophilic dyes, pigments and pearlescent agents, and their mixtures. Any colorant typically found in nail polish compositions can be used.

Suitable examples of fat-soluble dyes are, for example, Sudan red, DC Red 17, DC Green 6, β-carotene, soybean oil, Sudan brown, DC Yellow 11, DC Violet 2, DC Orange 5 and quinoline yellow.

Suitable pigments can be white or colored, inorganic and/or organic and coated or uncoated. Mention may be made, for example, of inorganic pigments such as titanium dioxide, optionally surface treated, zirconium or cerium oxides and iron or chromium oxides, manganese violet, ultramarine blue, chromium hydrate and ferric blue. Mention may also be made, among organic pigments, of carbon black, pigments of D & C type and lakes based on cochineal carmine or on barium, strontium, calcium or aluminum, such as D&C Red No. 10, 11, 12, and 13, D&C Red No. 7, D&C Red No. 5 and 6, and D&D Red No. 34, as well as lakes such as D&C Yellow Lake No. 5 and D&C Red Lake No. 2.

Suitable pearlescent pigments may also be included, and may be chosen from, for example, white pearlescent pigments, such as mica covered with titanium oxide or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride.

Color additives, such as natural extracts, may also be appropriate in various embodiments. One such example is spirulina paltensis extract, although other extracts may also be appropriate.

Preferably, a combination of dyes and particulates are utilized in order to provide both (a) coloring for the nail polish remover and (b) some degree of diffuse light scattering.

Surprisingly, it was found that adding a high load of colorants in a nail polish removing composition improves the user experience by lessening the perception of spent nail polish on the skin. According to certain embodiments, the total colorant is present in the nail polish removing formulation at an active concentration of between 0.5 wt % and 5.0 wt %. In other embodiments, the total colorant is present in an active concentration of between 0.5 wt % and 2.5 wt %. In other embodiments, the total colorant is present in an active concentration of between 0.5 wt % and 1 wt %. In other embodiments, one colorant is present at a concentration between 0.4 wt % and 5 wt %, or between 0.4 wt % and 2.5 wt %, or between 0.4 wt % and 1 wt %.

In various embodiments, the total colorant is present in an active concentration of at least 0.5 wt %, at least 1 wt %, or at least 2 wt %. In various embodiments, the total colorant is present in an active concentration of less than 5 wt %, or less than 4 wt %, or less than 2.5 wt %.

According to certain embodiments, more than one colorant is utilized, allowing the nail polish removing composition to absorb across a large portion of the visible light wavelengths, and preferably across the entire visible light spectrum, from 390 nm to 700 nm. According to certain embodiments, two or more colorants are utilized, and in other embodiments, three or more colorants are utilized. In certain preferred embodiments, one colorant is present in an amount at least 5 times that of any other colorant in the composition. In other preferred embodiments, one colorant is present in an amount greater than or equal to 0.5 wt %, and all other colorants are present in an amount less than 0.5 wt %.

Preferably, the colorants are selected such that the composition has a peak absorption in a portion of the visible light spectrum matching the color of the nail polish being removed. That is, that the color that the nail polish remover absorbs "matches" the color of the nail polish to be removed. For example, an embodiment to remove red nail polish would optically absorb red wavelengths, an embodiment to remove purple nail polish would optically absorb purple wavelengths, an embodiment to remove yellow nail polish would optically absorb yellow wavelengths, and so forth. In certain embodiments, kits are provided, utilizing a nail polish and a nail polish remover where the colorants are appropriately "matched" to the nail polish.

In certain embodiments, the nail polish removing composition has an absorbance peak at a wavelength between 390 nm and 700 nm. In other embodiments, at least one colorant has an absorbance peak at a wavelength between 390 nm and 700 nm.

Preferably, colorants are selected such that the nail polish removing composition has an absorption peak in a wavelength range of between 460 nm and 600 nm. More preferably, the colorants are also selected such that, in addition to the absorption peak between 460 nm and 600 nm, the nail polish removing composition also has a normalized extinction of at least 0.5 for at least one wavelength in the range when measured in an optically transparent solvent via spectrophotometer and across 1 cm path length in a ratio of 1:8 composition to optically transparent solvent (one part nail polish remover composition by weight out of eight, or 12.5% in water).

In other embodiments, the colorants are selected such that the nail polish removing composition has an extinction of at least 1.5 when measured across all wavelengths in the entire visible spectrum in an optically transparent solvent via spectrophotometer and across 1 cm path length in a ratio of 1:8 composition to optically transparent solvent.

Other Ingredients

The nail polish removing composition may optionally include other ingredients, such thickening agents, abrasive agents, fragrances, humectants, skin conditioning agents, surfactants, and preservatives.

Thickening Agent

In accordance with the present invention, compositions for removing nail polish, where the nail polish removing composition comprises at least one thickening agent are provided. Non-limiting examples of thickening agents that may be used according to various embodiments of the present invention include those conventionally used in cosmetics, such as polymers of natural origin and synthetic polymers. For example, nonionic, anionic, cationic, amphiphilic, and amphoteric polymers, and other known rheology modifiers, such as cellulose-based thickeners, may be used.

According to certain embodiments, the thickening agent may be an acrylic thickening agent (acrylic thickener) or an acrylamide thickening agent (acrylamide thickener). "Acrylic thickening agent" or "acrylic thickener" as used herein refers to polymers based upon one or more (meth) acrylic acid (and corresponding (meth)acrylate) monomers or similar monomers. "Acrylamide thickening agent" or "acrylamide thickener" as used herein refers to polymers based upon one or more acrylamide monomers or similar monomers.

According to certain embodiments, the thickening agent comprises at least one monomer performing a weak acid function such as, for example, acrylic acid, methacrylic acid, itaconic acid, crotonic acid, maleic acid and/or fumaric acid.

According to certain embodiments, the thickening agent comprises at least one monomer performing a strong acid function such as, for example, monomers having a function of the sulfonic acid type or phosphonic acid type, such as 2-acrylamido-2-methylpropane sulfonic acid (AMPS).

According to certain embodiments, the thickening agent may be crosslinked (or branched). Suitable examples of acceptable crosslinking agents include, but are not limited to, methylene bisacrylamide (MBA), ethylene glycol diacrylate, polyethylene glycol dimethacrylate, diacrylamide, cyanomethacrylate, vinyloxyethacrylate or methacrylate, formaldehyde, glyoxal, and compositions of the glycidylether type such as ethyleneglycol diglycidylether, or epoxides.

Suitable acrylic thickeners are disclosed in U.S. Patent Pub. Nos. 2004/0028637, entitled "Use as thickeners in cosmetics of neutralized copolymers comprising weak acid units and strong acid units, and cosmetic compositions comprising same," and 2008/0196174, entitled "Dyes for Keratinic Fibers Comprising a Special Anionic Thickener," the entire contents of both of which are incorporated herein by reference.

Specific non-limiting examples of suitable thickening agents include homopolymers or copolymers of acrylic or methacrylic acids or the salts thereof and the esters thereof, such as the products sold under the names VERSICOL F or VERSICOL K by Allied Colloid, ULTRAHOLD 8 by Ciba-Geigy, polyacrylates and polymethacrylates such as the products sold under the names LUBRAJEL and NORGEL by Guardian, or under the name HISPAJEL by Hispano Chimica, polyacrylic acids of SYNTHALEN K type, polyacrylamides, copolymers of acrylic acid and of acrylamide sold in the form of the sodium salt thereof, such as under the names RETEN by Hercules, the sodium polymethacrylate such as sold under the name DARVAN 7 by Vanderbilt, and the sodium salts of polyhydroxycarboxylic acids such as sold under the name HYDAGEN F® by Henkel, optionally crosslinked and/or neutralized 2-acrylamido-2-methylpropanesulphonic acid polymers and copolymers, for instance poly(2-acrylamido-2-methylpropanesulphonic acid) such as sold by Clariant under the name HOSTACERIN AMPS (INCI name: ammonium polyacryldimethyltauramide), crosslinked anionic copolymers of acrylamide and of AMPS, e.g. in the form of a water-in-oil emulsion, such as those sold under the name SEPIGEL 305 (INCI name: Polyacrylamide/C13-14 Isoparaffin/Laureth-7) and under the name SIMULGEL 600 (CTFA name: Acrylamide/Sodium acryloyldimethyltaurate copolymer/Isohexa-decane/Polysorbate 80) by SEPPIC, polyacrylic acid/alkyl acrylate copolymers of PEMULEN type, sodium acrylate/sodium acryloyldimethyl taurate such as that sold under the INCI name Sodium Acrylate/Sodium Acryloyldimethyl Taurate Copolymer & Hydrogenated Polydecene & Sorbitan Laurate & Trideceth-6 which is marketed by Lonza, Allendale, N.J., USA under the tradename ViscUpEZ. In certain embodiments, the thickening agent is selected from an acrylamide and a water soluble cellulose polymer (such as hydroxypropylmethylcellulose, ethylcellulose, and/or hydroxypropylcellulose), and combinations thereof.

According to certain embodiments, the thickening agent is a cellulose-based thickener. Suitable cellulose-based compounds include, but are not limited to, cellulose polymers, such as, for example, hydroxyethylcellulose, hydroxypropylcellulose, methylcellulose, and ethylhydroxyethylcellulose. Certain notable cellulose derivatives include hydroxyl-modified cellulose polymers such as Hydroxyethylcellulose, e.g., those having a molecular weight over 500,000 daltons such as NATROSOL 250 HHR and Hydroxypropyl cellulose, e.g., KLUCEL MF—both available from Ashland of Covington, Ky.

According to certain embodiments, the thickening agent is a polysaccharide. In general, polysaccharides may be divided into several categories. Polysaccharides that are suitable for use in the invention may be homopolysaccharides such as fructans, glucans, galactans and mannans or heteropolysaccharides such as hemicellulose. Suitable polysaccharides may be linear polysaccharides such as pullulan or branched polysaccharides such as gum arabic and amylopectin, or mixed polysaccharides such as starch.

According to certain embodiments, the thickening agent is an inorganic thickening agent. This may be an organoclay (hydrophobically treated clay), a hydrophilic clay, or other inorganic thickener.

The term "hydrophilic clay" means a clay that is capable of swelling in water; this clay is activated in water and forms after hydration a colloidal dispersion. These clays are products that are already well known per se, which are described, for example, in the book "Mineralogie des argiles", S. Caillere, S. Henin, M. Rautureau, 2nd edition 1982, Masson, the teaching of which is included herein by way of reference. Clays are silicates containing a cation that may be chosen from calcium, magnesium, aluminium, sodium, potassium and lithium cations, and mixtures thereof. Examples of such products that may be mentioned include clays of the smectite family such as montmorillonites, hectorites, bentonites, beidellites and saponites, and also of the family of vermiculites, stevensite and chlorites. These clays may be of natural or synthetic origin. Hydrophilic clays that may be mentioned include smectite products such as saponites, hectorites, montmorillonites, bentonites and beidellite. The term "lipophilic clay" (hydrophobically treated clay) means a clay that is capable of swelling in a lipophilic medium; this clay swells in activated in a hydrophobic solvent and thus forms a colloidal dispersion. Examples of lipophilic clays that may be mentioned include modified clays such as modified hectorite (Bentone Gel VCG from Elementis), and hectorites modified with a C10 to C22 fatty-acid ammonium chloride. Examples include hectorite modified with distearyldimethylammonium chloride (INCI name: disteardimonium hectorite).

In particular, among the thickening agents that may be used, mention may be made of silica particles. Suitable silicas include, but are not limited to, hydrophobic synthetic amorphous silicas, pyrogenic or fumed silica optionally with hydrophobic surface treatment with particle size less than 10 microns, such as less than 500 nm, such as less than 100 nm, such as from 5 nm to 30 nm, including all ranges and subranges therebetween. It is in fact possible to modify the surface of silica chemically, by a chemical reaction producing a decrease in the number of silanol groups present on the surface of the silica. The silanol groups can notably be replaced with hydrophobic groups: a hydrophobic silica is then obtained.

The at least one thickening agent may be present in the compositions of the present invention in an amount greater than 0.05% by weight, such as greater than 0.1% by weight, such as greater than 0.5% by weight, such as greater than 1% by weight and may be less than 15% by weight, including all ranges and subranges therebetween such as, for example, from 0.1% to 15%, such as from 0.1% to 10%, such as from 0.5% to 10%, such as from 0.75% to 7.5%, such as from 1% to 5%, etc., with all weights being based on the weight of the composition.

Abrasive Agents

In accordance with the present invention, compositions for removing nail polish, where the nail polish removing composition comprises at least one abrasive compound (abrasive system) are provided. A "abrasive compound" is a compound capable of providing abrasion or mechanical exfoliation and in accordance with the present invention has one or more of the following characteristics:

(1) Surface roughness: particles with irregular edges provide for abrasion;

(2) shape: the particles of the abrasive compound may have a non-angular shape such as a disc, oval or sphere;

(3) average particle size: in the context of abrasive compounds from mineral origins, shells, seeds micronized fruit kernel powders, and the like. The particles of the abrasive may have a particle size of 1000 microns ($\mu$m) or less, such as 500 $\mu$m or less, such as 300 $\mu$m or less, such as 150 $\mu$m or less, such as 75 $\mu$m or less, such as, 50 $\mu$m or less such as 30 $\mu$m or less; and (4) hardness: the abrasive particles may be soft so as to provide for mild abrasion.

According to certain embodiments, the abrasive of the present invention has at least two of the above-mentioned properties, such as at least three of the above-mentioned properties, such as all four of the above-mentioned properties. For example—the abrasive compound may be a large spherical material and not hard; or very small, hard, and having an irregular shape. The hardness may be between (inclusive of endpoints) 3-8 (Mohs hardness); or between 40-60 (Shore D hardness) if the compound is a wax or polymer.

The abrasive of the present invention may have at least two of the above-mentioned properties, such as at least three of the above-mentioned properties, and such as all four of the above-mentioned properties.

Suitable non-limiting examples of abrasive compounds include, but are not limited to, water-soluble abrasives such as sugars; and/or water-insoluble abrasives such as ground fruit kernel or shell powders, materials such as perlite, pumice or apricot kernel, coconut scrubs, zeolites, hydrated silica, calcium carbonate, dicalcium phosphate dihydrate, calcium pyrophosphate, alumina, sodium bicarbonate, polylactic acid, spherical waxes (for example, jojoba scrub beads), as well as synthetic polymeric materials such as polyethylene, polypropylene, polyethylene terephthalate, polymethlyl methacrylate or nylon.

The at least one abrasive compound may be present in the compositions of the present invention in an amount greater than 0.5% by weight, such as greater than 1% by weight, such as greater than 2.5% by weight, such as greater than 5% by weight such as less than 40% by weight, including all ranges and subranges therebetween such as, for example, from 0.5% to 40%, such as from 1% to 30%, such as from 2.5% to 25%, such as from 5% to 20%, etc., with all weights being based on the weight of the composition. However, it is to be understood that these weight amounts in this paragraph refer to the total amount of abrasive compound present, including those particles which particles of the abrasive compound used in accordance with the present invention which do not have the smoothness, shape, size and/or surface roughness characteristics discussed above.

Method of Use

Referring to FIG. 1, a method (100) for removing nail polish is also disclosed, utilizing the disclosed nail polish remover. The method begins (105) with the application (110) to a coated nail a nail polish removing composition that incorporates at least one solvent and at least one colorant, wherein the total concentration of colorant is between 0.5 wt % to 5.0 wt %. This application may be done with, e.g., a brush, a wipe, or simply by placing an amount of the composition on the nail and covering at least the nail with the composition. After application, the coated nail and nail polish removing composition are allowed (120) to remain in contact for a time sufficient to loosen the coating from the nail. Preferably, this is less than 5 minutes, and more preferably less than 1 minute. After this time has elapsed, the coating and the composition are then separated (130) from the nail itself, and the method ends (140). In some embodiments, one or more additional application cycles occurs.

Example 1

| Ingredient | wt % |
| --- | --- |
| Base | 95-100% |
| Propylene Carbonate | 20-40% |
| Ethanol | 20-40% |
| Glycerin | 15-30% |
| Thickening Agents | 1-5% |
| Abrasive Agents | 10-25% |
| Misc. (Oils, Filler, Water, etc.) | 0-10% |
| Colorants (Active) | 0-5% |

Figure 2:
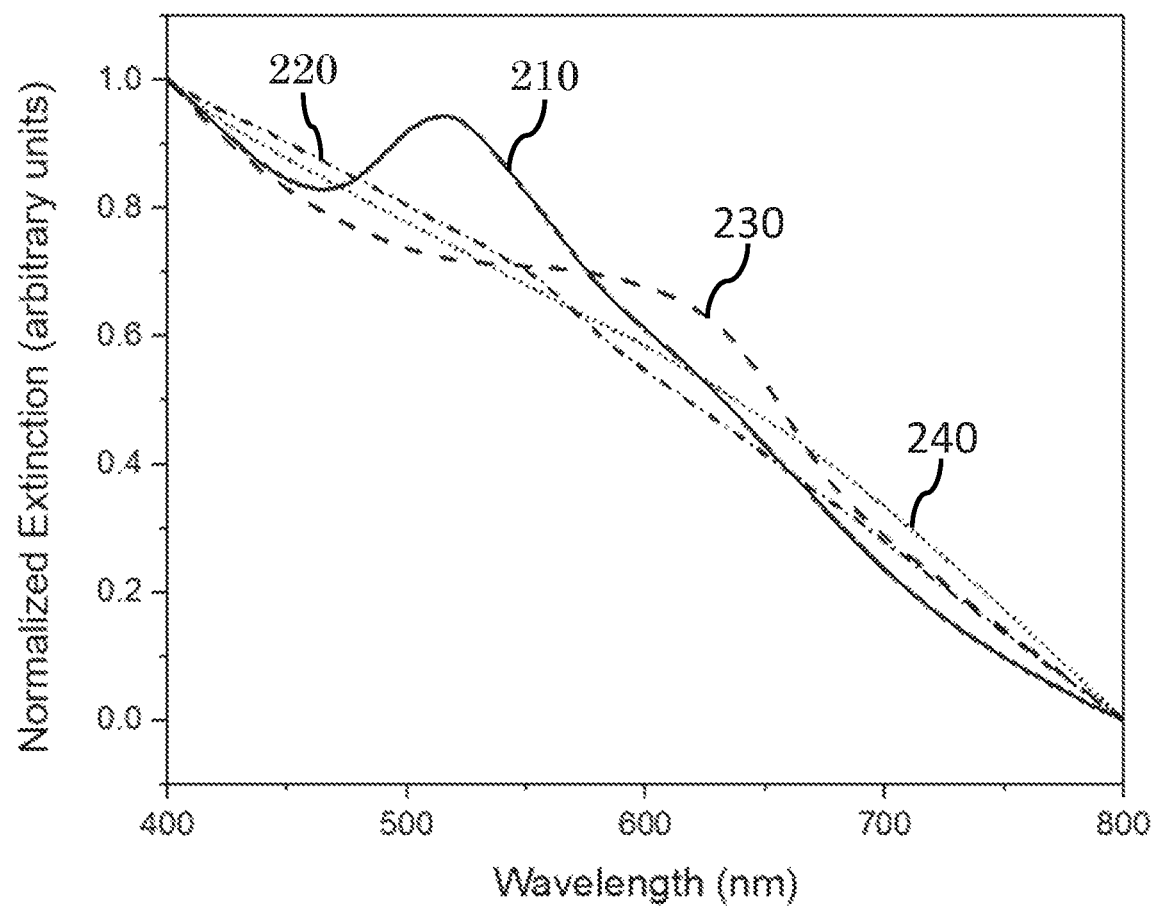
FIG. 2 is a graph illustrating normalized spectra for several nail polish removing compositions.

Referring to FIG. 2, An experiment was conducted to determine the impact of various colorants on optical density of compositions utilizing the above-described formulations. Utilizing an identical base, four variants were made using different pigments in a base such as Example 1. A first variant (210) utilized 0.5 wt % active of UNIPURE VIOLET LC 587 ultramarines pigment from Sensient Cosmetic Technologies, 0.035 wt % active of NATPURE AXP spirulina paltensis extract from Sensient Cosmetic Technologies and 0.2 wt % of CHROMA-LITE® Red CL4506 which is an effect pigment of mica, bismuth oxychloride, and iron oxides available from BASF. A second variant (220) utilized 0.12 wt % of CHROMA-LITE® Red and 0.025 wt % active TAO-77891 titanium dioxide from Miyoshi Kasei. A third variant (230) utilized 0.5 wt % active of NATPURE AXP spirulina paltensis extract from Sensient Cosmetic Technologies. A fourth variant (240) did not utilize any colorants. The extinction of each variant was then measured via spectrophotometer and across 1 cm path length in a ratio of approximately 1:8 of the composition to an optically transparent solvent (here, ethanol), and the normalized extinctions were plotted. As can be seen, the first variant is showing a peak at approximately 520 nm and has a normalized extinction of at least 0.5 for every wavelength in the range from 400-600 nm. None of the other variants exhibited a peak in the range of 400-600 nm, or specifically between 460-600 nm.

Example 2

| Variant # | 1 | 2 | 4 | 6 | 7 |
| --- | --- | --- | --- | --- | --- |
| Base | Example 1 | Example 1 | Example 1 | Ethanol | Ethanol |
| Iron Oxide | 0.05 | 0.03 | — | 0.05 | 0.03 |
| Spirulina Extract | 0.035 | | — | 0.035 | |
| Titanium Dioxide | | .025 | | | .025 |
| Ultramarines | 0.50 | | — | 0.50 | |
| Mica | 0.092 | 0.055 | — | 0.092 | 0.055 |
| Bismuth Oxychloride | 0.058 | 0.035 | — | 0.058 | 0.035 |

Additional experiments were conducted to further understand the impact of various colorants and bases on optical density of compositions utilizing the above-described formulations. Referring to the table above and FIG. 3, five variants were produced. The first three using an identical base to the one in Example 1, changing only the colorants. Variant 1 (310), is the same formula referred to for FIG. 2 (210). It exhibits a purple color, and as described above utilizes 0.5 wt % active of UNIPURE VIOLET LC 587 ultramarines pigment from Sensient Cosmetic Technologies, 0.2 wt % of CHROMA-LITE® Red CL4506 red iron oxide from BASF (0.05 wt % active red iron oxide, 0.92 wt % active mica, and 0.058 wt % active bismuth oxychloride), and 0.035 wt % active of NATPURE AXP spirulina paltensis as described in Example 1. Variant 2 (320) mirrors the formula used in FIG. 2 (220), exhibits an orange color, and utilizes 0.12 wt % of a CHROMA-LITE® Red CL4506 (0.03 wt % active red iron oxide, 0.55 wt % active mica, and 0.35 wt % active bismuth oxychloride) and 0.025 wt % active TAO-77891 titanium dioxide from Miyoshi Kasei. Variant 4 (330) utilized no colorant. Variant 6 (340) used the same pigments as Variant 1, but in ethanol, rather than the base used in Example 1. Similarly, Variant 7 (350) used the same pigments as Variant 2, but in ethanol rather than the Example 1 base. The extinction of each variant was then measured via spectrophotometer and across 1 cm path length in a ratio of approximately 1:8 of the composition to an optically transparent solvent (here, ethanol).

Figure 3:
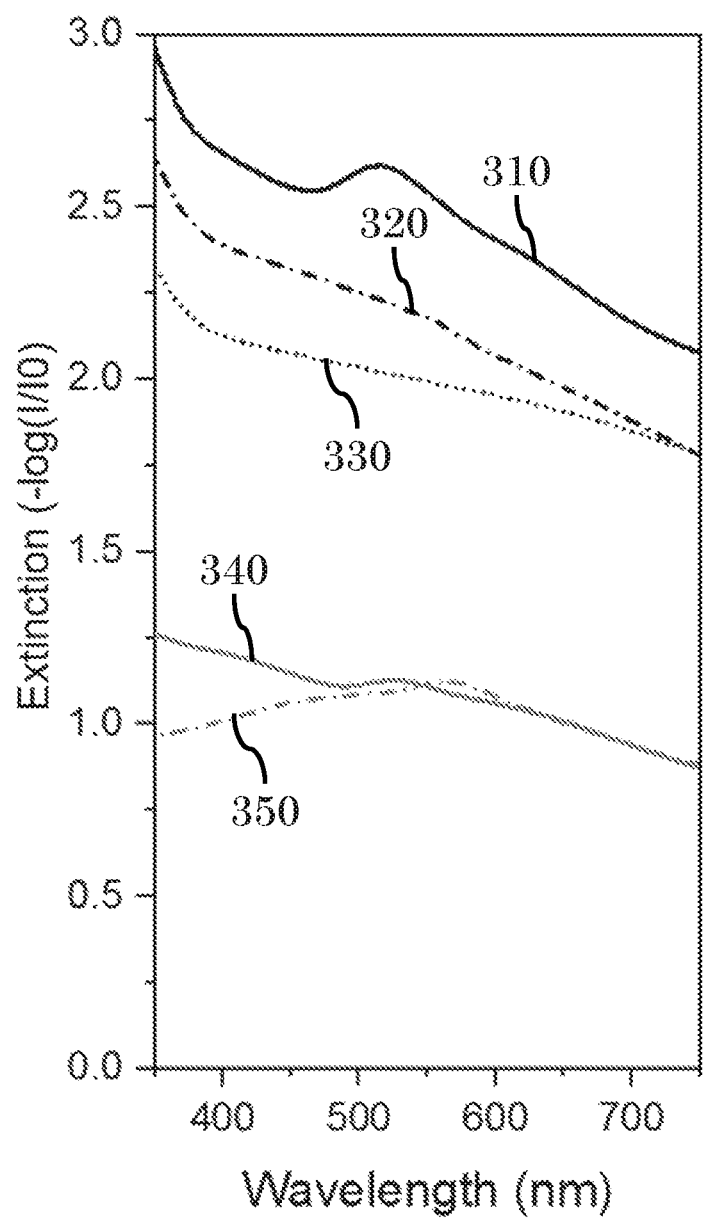
FIG. 3 is a graph illustrating spectra for several nail polish removing compositions.

Referring to FIG. 3, extinctions for each of the five variants is shown. The three variants using the Example 1 base (310, 320, 330) have the highest extinctions. The colorant-free variant, Variant 4 (330) has the lowest extinctions of the three variants, and shows no peaks across the visible light range, just a decrease in extinction as the wavelength increases. Variant 1 (310) has the highest extinction across the entire visible range and shows a peak at approximately 520 nm. Variant 5 (320) also has increased extinctions above the colorant-free variant across the entire visible range, although it does not have a peak around 520 nm. The two variants using ethanol as a base (340, 350) show dramatically different extinction profiles. Specifically, as compared to Variant 1 (310), Variant 6 (340) shows significantly reduced extinction, and now only shows a minor peak at about 530 nm. As compared to Variant 5 (320), Variant 7 (350) shows quite a different profile; there is now a peak at approximately 570 nm.

Those skilled in the art will recognize or be able to ascertain using no more than routine experimentation many equivalents to the specific embodiments of the invention described herein. Such equivalents are intended to be encompassed by the following claims.

What is claimed is:

1. A nail polish removing composition, comprising
at least one solvent; and
two or more colorants, wherein the two or more colorants have a total concentration of between 0.5 wt % to 5.0 wt %, wherein the two or more colorants comprises a first colorant, the first colorant being present in an amount of at least 5 times that of any other colorant in the nail polish removing composition,
wherein the nail polish removing composition has an absorption peak in a range between 460 nm and 600 nm, further wherein the nail polish removing composition has an extinction of at least 1.5 when measured across all wavelengths in the entire visible spectrum in an optically transparent solvent via spectrophotometer and across 1 cm path length in a ratio of 1:8 composition to optically transparent solvent.

2. The nail polish removing composition according to claim 1, where the at least one solvent is selected from the group consisting of acetone, an acetate, a low carbon alcohol, and a high boiling point ester.

3. The nail polish removing composition according to claim 1, wherein the nail polish removing composition is substantially free of acetone.

4. The nail polish removing composition according to claim 1, further comprising at least one thickening agent.

5. The nail polish removing composition according to claim 1, further comprising at least one abrasive agent.

6. A method of removing nail polish, comprising the steps of:
applying a nail polish removing composition according to claim 1 to a nail polish coated nail;
allowing the coated nail and nail polish removing composition to remain in contact for a time sufficient to loosen the coating from the nail, and separating the coating and the composition from the nail.

7. The nail polish removing composition according to claim 1, wherein the two or more colorants have a total concentration of at least 2 wt %.

* * * * *